United States Patent [19]

Portney

[11] Patent Number: 4,932,970
[45] Date of Patent: Jun. 12, 1990

[54] OPHTHALMIC LENS

[75] Inventor: Valdemar Portney, Irvine, Calif.

[73] Assignee: Allergan, Inc., Irvine, Calif.

[21] Appl. No.: 195,135

[22] Filed: May 17, 1988

[51] Int. Cl.$^5$ .......................... A61F 2/16; A61F 2/14; G02C 7/02; G02C 7/04

[52] U.S. Cl. ........................................ 623/6; 623/5; 351/160 R; 351/176

[58] Field of Search .................. 623/6, 5, 4; 351/176, 351/160 R, 160 H, 161, 160

[56] References Cited

U.S. PATENT DOCUMENTS

| | | | |
|---|---|---|---|
| 2,077,092 | 4/1937 | Broder | 351/176 |
| 3,735,685 | 5/1973 | Plummer | 351/176 X |
| 4,010,496 | 3/1977 | Neefe | 623/6 |
| 4,162,122 | 7/1979 | Cohen | 351/161 |
| 4,210,391 | 7/1980 | Cohen | 351/161 |
| 4,338,005 | 7/1982 | Cohen | 351/161 |
| 4,340,283 | 7/1982 | Cohen | 351/161 |
| 4,402,579 | 9/1983 | Poler | 623/6 X |
| 4,409,691 | 10/1983 | Levy | 623/6 |
| 4,500,382 | 2/1985 | Foster | 156/272.8 |
| 4,504,982 | 3/1985 | Burk | 623/6 |
| 4,673,406 | 6/1987 | Schlegel | 623/6 |
| 4,787,903 | 11/1988 | Grendahl | 623/6 |
| 4,828,558 | 5/1989 | Kelman | 623/6 |

FOREIGN PATENT DOCUMENTS

| | | |
|---|---|---|
| 3439551 | 4/1986 | Fed. Rep. of Germany . |
| WO86/03961 | 7/1986 | PCT Int'l Appl. .................... 623/6 |

OTHER PUBLICATIONS

Gupta, Pramod Kumar, Theoretical Analysis of the Fresnel Lens as a Function of Design Parameters, Applied Energy 0306-2619/81/0009-0301, 1981, pp. 302-310.

Egger, John R., Use of Fresnel Lenses in Optical Systems: Some Advantages and Limitations, SPIE vol. 193, Optical Systems Engineering, 1979, pp. 64-69.

Vanderwerf, Dennis, Approximating the Fresnel Lens, Electro-Optical Systems Design, Feb. 1982, pp. 47-52.

Farberov/Mironenko, Manufacturing Fresnel Lenses for Cameras, Sov. J. Opt. Technol. 50(3), Mar. 1983, pp. 186-188.

Primary Examiner—Ronald L. Frinks
Attorney, Agent, or Firm—Gordon L. Peterson; Loyal M. Hanson

[57] ABSTRACT

An ophthalmic lens having a size, shape, and composition adapted to be supported by the human eye in the optical path of the eye as an intraocular, contact, or corneal implant lens, includes a biocompatible lens body having a size and shape adapted to be supported by a human eye in the optical path of the eye. An optical portion of the lens body has anterior and posterior surfaces and a grooved portion defining a modified Fresnel or echelon lens pattern in at least one of the anterior and posterior surfaces. The modified echelon lens pattern includes annular zones that are configured so that at least some of the annular zones exhibit optical characteristics that vary circumferentially in order to at least partially correct for astigmatism.

32 Claims, 2 Drawing Sheets

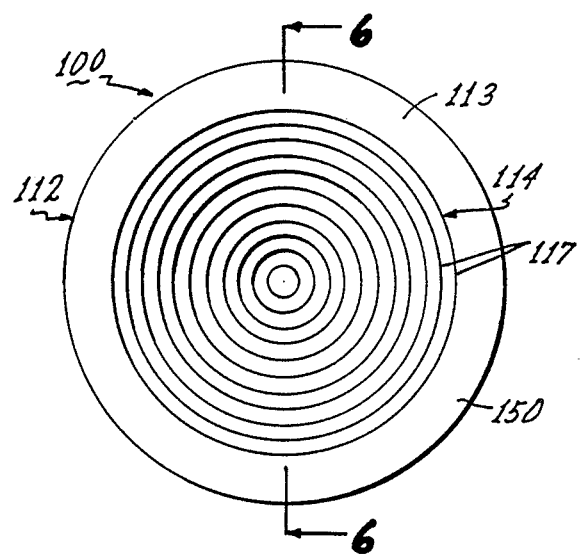
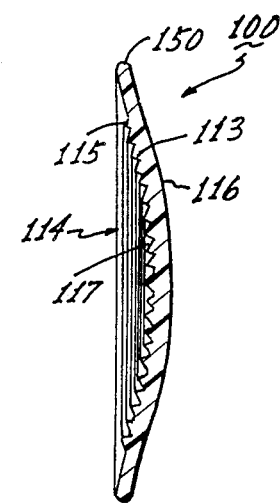
Fig.5
Fig.6
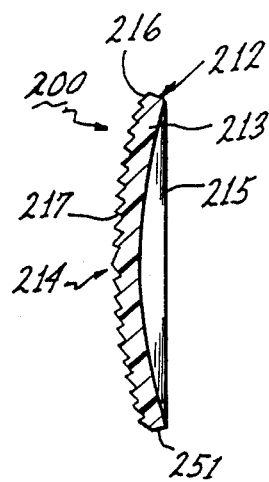
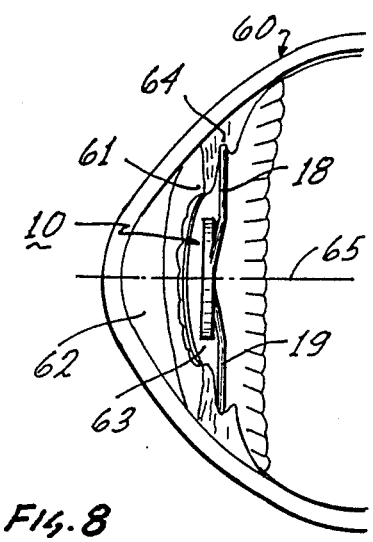
Fig.7
Fig.8

OPHTHALMIC LENS

BACKGROUND OF THE INVENTION

1. Technical Field

This invention relates generally to lenses, and more particularly to an ophthalmic lens providing astigmatism correction.

2. Background Information

Ophthalmic lenses include intraocular lenses (IOL's), contact lenses, and corneal implant lenses. Each of these has an optical portion with anterior and posterior surfaces, and some means for use in supporting the optical portion on the eye.

An IOL, for example, may include resilient fixation members projecting radially from the optical portion that support the lens within the posterior or anterior chambers of the eye. Contact lenses, on the other hand, have a curved posterior surface which adapts them to be retained by the surface tension of tears, and corneal implant lenses commonly include a peripheral portion that is implanted in a pocket formed in the cornea.

Apart from these differences, the lenses serve a similar function. They help focus impinging light on the retina according to the refractive index of the lens material and the radius of curvature of the lens surface. In doing this, they may sometimes provide astigmatism correction as well.

In many cases, however, an undesirably thick lens is required to produce the optical characteristics desired so that the lens may be thicker or heavier than desired for satisfactory retention on the eye. In addition, high refractive index materials may be less nutrient permeable.

A corneal implant lens, for example, may be implanted by removing a forward portion of the cornea and suturing it back on over the lens. Thus, lightness, thinness, and nutrient permeability are desired. For another example, the implantation of soft IOL's often involves folding the lens to facilitate insertion into the eye and occasional refolding under certain circumstances dictating removal. Thus, thinness for folding purposes is desired as well.

In this regard, German Patent No. DE 3439551 Al describes a one-piece natural lens substitute that can be folded for insertion into the anterior or posterior chamber of the eye. It employs a conventional Fresnel lens pattern that includes individual periaxial annular zones separated by steps. The radii of curvature of the individual zonal areas are selected so that the focal points of all zones coincide, and this results in a thinner, foldable lens.

Although effective in some respects for reducing lens thickness, the Fresnel lens pattern does not provide the astigmatism correction often desired. Thus, there is a need for an ophthalmic lens having attributes of lightness, thinness, and, for some applications, foldability, while providing astigmatism correction.

SUMMARY OF THE INVENTION

This invention solves the problems outlined above by providing an ophthalmic lens having a modified Fresnel lens pattern--modified to include at least some annular zones configured to exhibit optical characteristics that vary circumferentially in order to correct for astigmatism.

Thus, the lens can be made light, thin, foldable, and nutrient permeable, and still provide desired optical characteristics, including astigmatism correction, for vision correction purposes.

Generally, an ophthalmic lens constructed according to the invention includes a biocompatible lens body having a size and shape adapted to be supported by a human eye in the optical path of the eye, which lens body has an optical portion with anterior and posterior surfaces.

According to a major aspect of the invention, the optical portion has a grooved portion defining a modified echelon lens pattern in at least one of the anterior and posterior surfaces. The modified echelon lens pattern includes annular zones, at least some of which are configured to exhibit optical characteristics that vary circumferentially in order to at least partially corrects for astigmatism.

According to another aspect of the invention, the ophthalmic lens includes retaining means for use in retaining the lens on the eye. This may be a separate fixation member attached to an intraocular lens body for use in retaining the lens in the anterior or posterior chambers of the eye.

The grooved portion may be located in the anterior surface or the posterior surface, and the modified echelon lens pattern may take the form of annular prismatic grooves that cover substantially all of the optical portion of the lens.

The above-mentioned and other objects and features of this invention and the manner of attaining them will become apparent, and the invention itself will be best understood, by reference to the following description of an embodiment of the invention taken in conjunction with the accompanying drawings.

BRIEF DESCRIPTION OF THE DRAWINGS

FIG. 5 illustrates a contact lens according to the invention with a concave posterior surface defining the modified echelon lens pattern;

FIG. 6 is a cross sectional view taken on line 6-6 of FIG. 5;

FIG. 7 is a cross sectional view of a corneal implant lens having a convex anterior surface defining the echelon lens pattern; and FIG. 8 is a cross sectional view of the eye with the intraocular lens of FIG. 1 shown retained in the posterior chamber.

DESCRIPTION OF THE PREFERRED EMBODIMENTS

Figure 1:
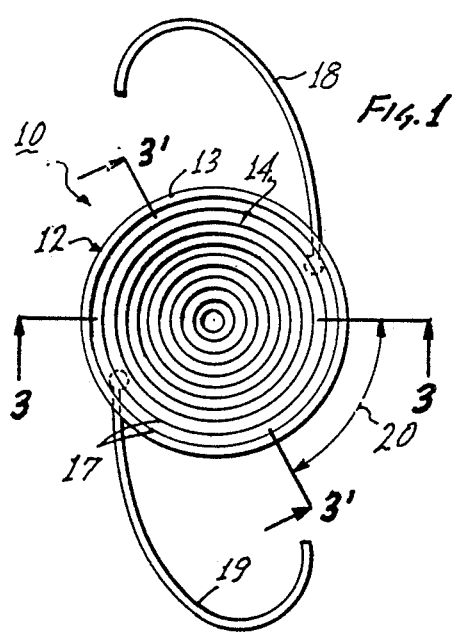
FIG. 1 of the drawings is a plan view of an intraocular lens having separate fixation members for use in retaining the lens in the posterior chamber of the eye.

Referring now to the drawings, there are shown three versions of an ophthalmic lenses constructed according to the invention, intraocular lens 10 (FIGS. 1-4 and 8), contact lens 100 (FIGS. 5 and 6), and corneal implant lens 200 (FIG. 7). Generally, these lenses include a biocompatible lens body, an optical portion of the lens body, and a grooved portion of the optical portion defining a modified echelon lens pattern.

In each case, the lens body has a general size shape, and composition adapted to be supported in contact with a human eye in the optical path. It is similar in some respects to known lenses, the lens body being suited for the particular type of application, such as intraocular, contact, or corneal implant. In this regard, the lens body may be composed of any of the various materials used for known lenses.

Similarly, the optical portion of the lens body is in some respects comparable to existing lenses. Preferably, it encompasses most or all of the lens body and provides desired optical characteristics for vision correction purposes. It may cover just a central region of the lens body, or an annular region or other segment.

The grooved portion of the optical portion is different, however. It incorporates a modified Fresnel or echelon lens pattern having the desired optical characteristics. This achieves a significant reduction in lens thickness and weight and a corresponding increase in flexibility, while at least partially correcting for astigmatism with an ophthalmic lens.

The echelon lens pattern includes "annular zones", that term including annular segments or zones that do not extend a full three hundred sixty degrees. In other words, an echelon lens pattern employing segments is within the scope of the inventive concepts disclosed and claimed. These annular zones are modified as compared to a conventional echelon lens pattern in the sense that at least some are configured to exhibit optical characteristics that vary circumferentially around the annular zones for astigmatism correction purposes.

Figure 2:
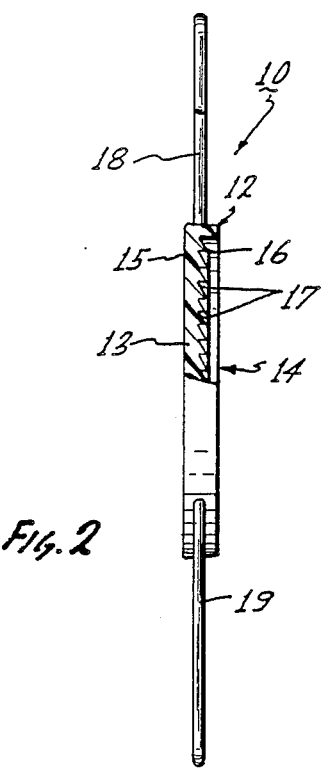
FIG. 2 is a side view of the intraocular lens.
Figure 3:
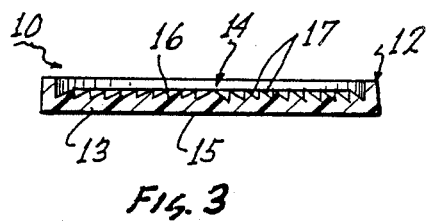
FIG. 3 is a cross sectional view of the intraocular lens taken on line 3—3 of FIG. 1.

Considering first the intraocular lens 10 illustrated in FIGS. 1-3, it includes a circular lens body 12, a circular optical portion 13, and a grooved portion 14 that defines the modified echelon lens pattern. The optical portion 13 in the illustrated embodiment covers the entire lens body and it has a posterior surface 15 and an anterior surface 16 (FIGS. 2 and 3).

The grooved portion 14 includes a series of annular concentric prismatic grooves 17 in the anterior surface 16 that divide the optical portion 13 into annular zones (the region between grooves). These define the modified echelon lens pattern which can partially or completely cover the optical portion 13. The grooves 17, although preferably circular, can have other configurations, such as oval, depending on the precise application. Preferably, the resulting annular zones extend a full three hundred sixty degrees, although they may extend less than that.

Fixation members 18 and 19 extend radially from the lens body 12. These serve as retaining means for use in retaining the lens 10 on the eye within the posterior chamber of the eye. They may be configured and attached utilizing structure similar to that described in United States Patent Application Ser. No. 804,674 filed Dec. 4, 1985, now U.S. Pat. No. 4,834,751 and United States Patent Application Ser. No. 096,747 filed Sept. 15, 1987, now U.S. Pat. No. 4,790,846. Those applications are incorporated by reference for the structural details provided in that regard.

The lens 10 is composed of a foldable material, and it is folded and inserted into the eye, with the fixation members 18 and 19 being then seated in one or both of the ciliary sulcus and the capsular bag so that the optical portion lies in the optical path of the eye with the central axis of the optical portion 13 substantially coaxial with the optical axis of the eye. In this position, incident light rays pass through the lens, refracted along the way according to the modified echelon lens pattern.

The series of concentric grooves 17 forming the modified echelon lens pattern are spaced apart and individually shape according to known techniques to achieve the desired optical characteristics. They form a modified Fresnel or echelon lens pattern in the sense that they are somewhat like a conventional Fresnel or echelon lens pattern but sufficiently different to correct for astigmatism. Like a conventional echelon lens pattern they form a series of discrete prismatic surfaces or echelon surfaces that cooperatively direct incident light rays generally toward a common focus, thereby approximating a continuous lens surface while eliminating lens bulk. But unlike the conventional echelon lens pattern, they are configured to vary in optical characteristics circumferentially for astigmatism correcting purposes.

In other words, at least some of the annular zones exhibit optical characteristics that vary for different values of an angle 20 in FIG. 1. This is done so that each prismatic surface approximates a corresponding segment on the surface of a conventional astigmatism correcting lens, so that together they achieve characteristics similar to those of the conventional astigmatism correcting lens without the lens bulk needed to define the usual curved lens surface.

Figure 4:
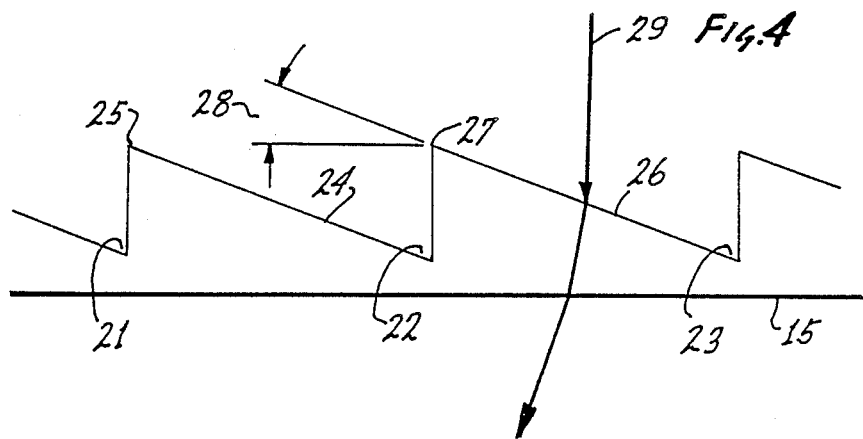
FIG. 4 is a diagrammatic view showing an enlarged portion of the cross sectional view of FIG. 3.

FIG. 4 further illustrates this aspect in diagrammatic form. It depicts an enlarged portion of the cross sectional view of FIG. 3, and it includes a series of grooves 21-23 that represent specific ones of the series of grooves 17 in FIGS. 1-3. The grooves 21 and 22 result in a prismatic surface or step 24 extending from the groove 22 to an apex 25, and the grooves 22 and 23 result in a prismatic surface or step 26 extending from the groove 23 to an apex 27, the apexes 25 and 27 defining the anterior surface 16 referred to above that is designated in FIGS. 2 and 3.

The distance between adjacent apexes, such as between the apex 25 and the apex 27, is the groove width, and with currently available fabrication techniques this may be on the order of 0.1 to 0.5 millimeter or less. This results in a groove frequency of two to ten grooves per millimeter or more, and a correspondingly sharp image despite the discrete steps of the modified echelon lens pattern.

Each step, such as the step 26, is inclined relative to the optical axis to approximate a corresponding segment on the surface of a conventional astigmatism correcting lens having the desired characteristics. This results in an apex angle 28 which varies for different meridians for astigmatism correcting purposes so that the step 26 exhibits optical characteristics that vary for different values of the angle 20 in FIG. 1.

The variation can be generally continuous or include step variations without departing from the inventive concepts disclosed. In addition, the grooves can be configured so that optical characteristics vary radially from step to step (groove to groove) also, to achieve other desired optical characteristics. Incident light rays, such as a ray 29, are refracted accordingly toward a focal point which, when the IOL is implanted, lies substantially at the retina.

The foregoing illustrates the manner in which the ophthalmic lens of this invention achieves a far thinner profile while correcting for astigmatism. The particulars of echelon lens design are well developed in the art, and they are not discussed in further detail. They are utilized to produce an apex angle that varies circumferentially as described above for astigmatism correcting purposes.

Fabrication of the intraocular lens 10 proceeds accordingly using known techniques, such as precision molding and laser etching. It may be of known composition, such as a silicone, polyurethane, or polymethylmethacrylate material.

The contact lens 100 in FIGS. 5 and 6 is similar to the intraocular lens 10 in several respects, and some reference numerals are increased by 100 over those designating similar features in FIGS. 1-3. The contact lens 100 includes a circular lens body 112, a circular optical portion 113, and a grooved portion 114 of the optical portion that defines a series of annular concentric grooves 117 in the form of a modified echelon lens pattern.

The lens body has a size, shape, and composition adapted to be used as a contact lens. It is similar in this respect to conventional contact lenses, and is fabricated using known techniques using an oxygen permeable material such as a polyhydroxyethylmethachrylate material, commonly called "phema," or a vinylpylrolidone/methylmethachrylate material, commonly called "vp/mma." A relative hard, gas permeable material, such as a silicone acrylate material, may also be used.

The optical portion 113 has a concave posterior surface 115 and a convex anterior surface 116. In use, the posterior surface 115 faces the cornea of the eye, the curved posterior surface serving as means for use in retaining the lens 100 on the eye by surface tension of tears.

The grooved portion 114 is formed in the posterior surface so that there is a generally uniform environment presented to the modified echelon lens pattern, i.e. the tears. Thus, optical characteristics can be better predicted. In addition, the optical portion 113 encompasses only a portion of the lens body 112, there being an annular outer portion 150 that lies beyond the optical path of the eye.

The corneal implant lens 200 in FIG. 7 is also similar in many respects to the intraocular lens 10, and some reference numerals are increased by 200 over those designating similar features in FIGS. 1-3. It includes a lens body 212, a circular optical portion 213, and a grooved portion 214 of the optical portion that defines a series of annular concentric grooves 217 in the form of a modified echelon lens pattern.

The lens body has a size, shape, and composition adapted to be used as a corneal implant lens. It is similar in this respect to conventional corneal implant lenses, and is fabricated according to known techniques using a glucose permeable material, such as a polyhydroxyethylmethacrylate material or a vinylpylrolidone/methylmethachrylate material.

The optical portion 213 includes a concave posterior surface 215 and a convex anterior surface 216. It encompasses a substantial portion of the lens body 212, extending to a periphery portion 251 that is placed in a pocket in the cornea where it serves as means to retain the corneal implant lens 200 on the eye. The series of grooves 217 are formed in the anterior surface 216 so that they face outwardly from the eye when the lens is implanted, away from sensitive tissue.

Considering now FIG. 8, there is shown the intraocular lens 10 in place within eye 60, accomplished according to the method of correcting vision of the invention. The method includes providing an ophthalmic lens having a modified echelon lens pattern, and retaining the ophthalmic lens in the optical path of the eye. The lens 10 is implanted according to these steps.

Iris 61 lies between anterior chamber 62 and posterior chamber 63, and the lens 10 is mounted within the posterior chamber with the fixation members 18 and 19 seated in the ciliary sulcus 64. In this position, the lens 10 lies in the optical path or axis 65 of the eye, where the modified echelon lens pattern directs incident light to a desired focus on the retina of the eye, doing so with a far thinner profile than conventional lenses.

Retention of the lens 10 on the eye 60 illustrates the manner in which IOL's are often implanted to correct vision loss due to cataracts, the natural lens of the eye being removed. An ophthalmic lens according to this invention can also be used to correct vision loss due to other causes, such as high myopia. The lens is implanted in the anterior chamber without removing the natural lens to compensate for extreme nearsightedness. In addition, the ophthalmic lens of this invention can be used in circumstances where an ineffective IOL already implanted within the eye might otherwise have to be removed to make room for a replacement and such removal is considered difficult or dangerous.

Because the lens 10 is so much thinner, it can be implanted in the eye adjacent an IOL that was previously implanted. For example, if the IOL previously implanted is in the posterior chamber, the IOL of this invention may be implanted in the anterior chamber. Thus, the difficult and risky procedure of removing the previously implanted IOL is avoided.

Furthermore, the lens can be made light, thin, foldable, and nutrient permeable, and still provide desired optical characteristics, including astigmatism correction, for vision correction purposes.

As various other changes may be made in the form, construction, and arrangement of the described components without departing from the spirit and scope of the invention and without sacrificing any of its advantages, all matter herein is to be interpreted as illustrative and not in any limiting sense.

What is claimed is:

1. An ophthalmic lens, comprising:
   a biocompatible lens body having a size and shape adapted to be supported in contact with a human eye in the optical path of the eye;
   the lens body having an optical portion with anterior and posterior surfaces;
   the optical portion having a grooved portion defining a modified echelon lens pattern in at least one of the anterior and posterior surfaces; and
   the modified echelon lens pattern including annular zones that are configured so that at least some of the annular zones exhibit optical characteristics that vary circumferentially in order to at least partially correct for astigmatism.

2. An ophthalmic lens as recited in claim 1, further comprising:
   retaining means for use in retaining the lens on the eye.

3. An ophthalmic lens as recited in claim 2, wherein the retaining means includes:
   a separate fixation member attached to the lens body.

4. An ophthalmic lens as recited in claim 2, wherein:
   the lens body has a size and shape adapted to be inserted in the anterior chamber of the eye as an intraocular lens; and
   the retaining means includes a fixation member extending generally radially from the lens body.

5. An ophthalmic lens as recited in claim 2, wherein:
the lens body has a size and shape adapted to be inserted in the posterior chamber of the eye as an intraocular lens; and
the retaining means includes a fixation member extending generally radially from the lens body.

6. An ophthalmic lens as recited in claim 1, wherein:
the lens body is composed of a polymethylmethacrylate material.

7. An ophthalmic lens as recited in claim 1, wherein:
the lens body is composed of a resilient material that can be folded for implantation purposes.

8. An ophthalmic lens as recited in claim 7, wherein:
the lens body is composed of a material selected from the group consisting of a silicone material and a polyurethane material.

9. An ophthalmic lens as recited in claim 2, wherein:
the lens body has a size and shape adapted to be placed against the eye as a contact lens; and
the retaining means includes a curved portion of the posterior surface adapted to be retained against the eye by surface tension of tears.

10. An ophthalmic lens as recited in claim 9, wherein:
the lens body is composed of an oxygen permeable material.

11. An ophthalmic lens as recited in claim 10, wherein:
the lens body is composed of a material selected from the group consisting of a polyhydroxyethylmethachrylate material, a vinylpylrolidone/methylmethachrylate material, and a silicone acrylate material.

12. An ophthalmic lens as recited in claim 2, wherein:
the lens body has a size, shape, and composition adapted to be implanted in the cornea of the eye as a corneal implant lens; and
the retaining means includes a periphery portion of the lens body adapted to be retained within a pocket formed in the cornea of the eye.

13. An ophthalmic lens as recited in claim 12, wherein:
the lens body is composed of a glucose permeable material.

14. An ophthalmic lens as recited in claim 13, wherein:
the lens body is composed of a material selected from the group consisting of a polyhydroxyethylmethachrylate material and a vinylpylrolidone/methylmethachrylate material.

15. An ophthalmic lens as recited in claim 1, wherein:
the grooved portion is in the anterior surface.

16. An ophthalmic lens as recited in claim 1, wherein:
the grooved portion is in the posterior surface.

17. An ophthalmic lens as recited in claim 1, wherein:
the modified echelon lens pattern includes a series of concentric prismatic grooves.

18. An ophthalmic lens as recited in claim 17, wherein:
the prismatic grooves define step widths less than 0.5 millimeter.

19. An ophthalmic lens as recited in claim 1, wherein:
the one of the anterior and posterior surfaces in which the modified echelon lens pattern is defined is concave.

20. An ophthalmic lens as recited in claim 1, wherein:
the one of the anterior and posterior surfaces in which the modified echelon lens pattern is defined is convex.

21. An ophthalmic lens as recited in claim 1, wherein:
the modified echelon lens pattern includes annular grooves.

22. An ophthalmic lens as recited in claim 1, wherein the annular zones extend substantially 360 degrees.

23. An ophthalmic lens as recited in claim 1, wherein:
the modified echelon lens pattern covers substantially all of the optical portion.

24. An intraocular lens, comprising:
a body of transparent, resilient material defining a lens body that can be folded for implantation purposes, the lens body having a size, shape, and composition adapted to be implanted in the eye;
an optical portion of the lens body having anterior and posterior surfaces;
a grooved portion of the optical portion defining a modified echelon lens pattern in one of the anterior and posterior surfaces;
the modified echelon lens pattern including annular zones that are configured so that at least some of the annular zones exhibit optical characteristics that vary circumferentially in order to at least partially correct for astigmatism; and
retaining means, including a separate fixation member extending outwardly from the lens body for use in retaining the in the eye.

25. An ophthalmic lens, comprising:
a body of transparent, resilient material defining a lens body having, a size, shape, and composition adapted to be supported in contact with a human eye in the optical path of the eye;
an optical portion of the lens body having an anterior surface and a posterior surface;
a grooved portion of the optical portion defining a modified echelon lens pattern in at least one of the anterior and posterior surfaces; and
at least one echelon surface in the modified echelon lens pattern being inclined relative to an optical axis of the lens an amount that varies circumferentially for astigmatism correction purposes.

26. A method of correcting vision, comprising:
providing an ophthalmic lens having an echelon lens pattern modified to provide suitable optical characteristics for at least partially correcting for astigmatism; and
retaining the ophthalmic lens in contact with the eye in the optical path of an eye.

27. A method as recited in claim 26, further comprising:
implanting the ophthalmic lens in the eye.

28. A method as recited in claim 27, further comprising:
removing the natural lens of the eye.

29. A method as recited in claim 27, further comprising:
implanting the ophthalmic lens in the eye without removing the natural lens of the eye.

30. A method as recited in claim 26, wherein:
the ophthalmic lens is an intraocular lens; and
the step of retaining includes implanting the intraocular lens in the eye of a patient having a previously implanted lens in the eye without removing the previously implanted lens.

31. A method of correcting astigmatic vision, comprising:
providing an ophthalmic lens having a modified echelon lens pattern defining at least one echelon surface that is inclined relative to an optical axis of the lens an amount that varies at different meridians to provide suitable optical characteristics for at least partially correcting astigmatic vision of an eye; and retaining the ophthalmic lens on the eye in the optical path of the eye.

32. An ophthalmic lens as recited in claim 2, wherein: the lens body has a size and shape adapted to be inserted in the anterior chamber of the eye without removing the natural lens; and the retaining means includes a fixation member extending generally radially from the lens body.

* * * * *

UNITED STATES PATENT AND TRADEMARK OFFICE
CERTIFICATE OF CORRECTION

PATENT NO. : 4,932,970

DATED : June 12, 1990

INVENTOR(S) : Valdemar Portney

It is certified that error appears in the above-identified patent and that said Letters Patent is hereby corrected as shown below:

```
Column 8, line 24 delete "retaining means, including".
Column 8, line 24 delete "separate".
Column 8, line 26 after "retaining the" insert -- lens --.
```

Signed and Sealed this

Eighteenth Day of February, 1992

Attest:

HARRY F. MANBECK, JR.

*Attesting Officer*   *Commissioner of Patents and Trademarks*